United States Patent [19]

Bezoari

[11] Patent Number: 4,745,206

[45] Date of Patent: May 17, 1988

[54] AMINOPHENOXYPHOSPHAZENES AND A PROCESS FOR PRODUCING SAME

[75] Inventor: Massimo D. Bezoari, Baton Rouge, La.

[73] Assignee: The Dow Chemical Company, Midland, Mich.

[21] Appl. No.: 868,972

[22] Filed: May 30, 1986

[51] Int. Cl.$^4$ ............................................... C07F 9/24
[52] U.S. Cl. ................................................... 558/080
[58] Field of Search ........................................... 558/80

[56] References Cited

U.S. PATENT DOCUMENTS

| | | | |
|---|---|---|---|
| 3,206,494 | 9/1965 | Lund et al. | 558/80 |
| 3,240,728 | 3/1966 | Lund | 260/2.5 |
| 3,446,876 | 5/1969 | Breslow | 558/80 |
| 4,029,634 | 6/1977 | Meredith | 260/45.9 NP |
| 4,107,108 | 8/1978 | Dieck et al. | 521/85 |
| 4,117,041 | 9/1978 | Guechl | 260/927 N |
| 4,124,557 | 11/1978 | Dieck et al. | 260/30.6 |
| 4,179,555 | 12/1979 | Cheng et al. | 528/168 |
| 4,440,921 | 4/1984 | Allcock et al. | 528/168 |

FOREIGN PATENT DOCUMENTS 320498  11/1971  U.S.S.R. .................. 558/80

OTHER PUBLICATIONS

Kajiwara et al., "Phosphonitrilic Chloride: 23, Substitution Reaction of Phosphonitrilic Chloride Trimer with Sodium Hydroxymethylphenolate and Polymerization of Substitution Products", Polymer, 1975, vol. 16, Jan. 21–24.

Kumar, Devendra, et al., "High-Strength Fire-and Heat-Resistant Imide Resins Containing Cyclotriphosphazene and Hexafluoroisopropylidene Groups," Journal of Polymer Science, vol. 22, John Wiley & Sons, Inc. (1984), pp. 927–943.

Kumar, Devendra, "Polybismaleimide Containing Tetrakisphenoxycyclotriphosphazenes," Journal of Polymer Science, vol. 23, John Wiley & Sons, Inc. (1985), pp. 1661–1670.

*Primary Examiner*—Anton H. Sutto
*Attorney, Agent, or Firm*—James M. Pelton

[57] ABSTRACT

This invention relates to phenoxy- and isopropoxyaminophenoxycyclotriphosphazenes and to a process for their preparation. The process comprises reacting R-chlorocyclotriphosphazene with an inorganic salt of aminophenoxide. The reaction takes place in the presence of an inert organic solvent and at a temperature within the range of from about 20° C. to about 150° C.

23 Claims, No Drawings

AMINOPHENOXYPHOSPHAZENES AND A PROCESS FOR PRODUCING SAME

BACKGROUND OF THE INVENTION

This invention relates to isopropoxy- and phenoxyaminophenoxycyclotriphosphazenes and to a process for producing same.

It is reported by Kumar et al in "High-Strength Fire- and Heat-Resistant Imide Resins Containing Cyclotriphosphazene and Hexafluoroisopropylidene Groups", *Journal of Polymer Science*, Volume 22, pages 927–943 (1984), John Wiley & Sons, Inc., that triphenoxy-tris-(aminophenoxy)cyclotriphosphazenes are used as intermediates to produce maleimidophenoxycyclotriphosphazenes which are linked by hexafluoroisopropylidenediphthalimide groups to yield high strength, fire- and heat-resistant polymers. In "Polybismaleimide Containing Tetrakisphenoxycyclotriphosphazenes", D. Kumar, *Journal of Polymer Science*, Volume 23, pages 1661–1670 (1985), John Wiley & Sons, Inc., it is reported that tetraphenoxy-bis(aminophenoxy)cyclotriphosphazene is an intermediate used in the production of tetraphenoxy-bismaleimidocyclotriphosphazene which is polymerizable to produce a heat-resistant polymer.

Not only are these phenoxyaminophenoxycyclotriphosphazene compounds useful as intermediates, but it has also been found that they exhibit flame-retardant properties in flexible foam compositions.

The processes described for producing triphenoxy-tris(aminophenoxy)cyclotriphosphazene and tetraphenoxy-bis(aminophenoxy)cyclotriphosphazenes can generally be described by the two-step sequence of: (1) reacting triphenoxy-trichlorocyclotriphosphazene, in the case of synthesizing the former, and tetraphenoxy-dichlorocyclotriphosphazene, in the case of synthesizing the latter, with sodium nitrophenoxide. The resultant products are, respectively, triphenoxy-tris(nitrophenoxy)cyclotriphosphazene and tetraphenoxy-bis(nitrophenoxy)cyclotriphosphazene. These products are then subjected to catalytic hydrogenation by contacting same with a catalyst, such as platinum oxide, in the presence of hydrogen gas. While these processes achieve their intended purpose, they are disadvantaged in that they are multistepped, require an expensive catalyst and use an explosive gas, i.e., hydrogen.

It is therefore an object of this invention to provide a noncatalytic one-step process for the production of isopropoxy- and phenoxy-aminophenoxycyclotriphosphazenes. The process does not involve the use of hydrogen gas.

The Invention

This invention relates to a process for the production of aminophenoxycyclotriphosphazenes of the formula:

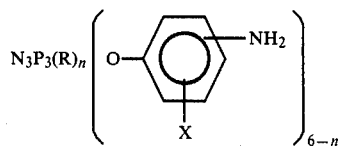

wherein R is an isopropoxy radical of the formula

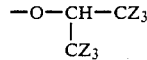

or an aryloxy radical of the formula,

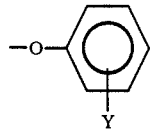

wherein each Z constituent is independently selected from F and H, wherein X and Y are each independently selected from Cl, Br, F and H, and wherein n is a whole integer which is $\geq 1$ and $\leq 5$. The process comprises reacting an R-chlorocyclotriphosphazene having n R constituents and (6-n) chloride constituents with an inorganic salt of aminophenoxide for a time period sufficient to yield the desired aminophenoxycyclotriphosphazene. The reaction occurs in the presence of an inert, organic solvent medium and at a temperature within the range of from about 20° C. to about 150° C. The molar ratio of the R-chlorocyclotriphosphazene reactant to the inorganic salt of aminophenoxide is 1:a, wherein a is greater than 5-n. Improved yields—indeed, yields up to 100%—can be achieved if the molar ratio is 1:6-n or above. (The yield is based upon NMR analysis of the reaction mix.)

The subject process may be represented by:

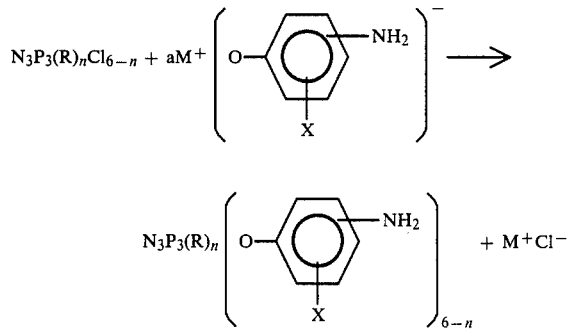

wherein a is greater than 5-n and $M^+$ is an inorganic cation, preferably a metal such as Na, K, and the like.

This invention also relates to compounds of the following formulas:

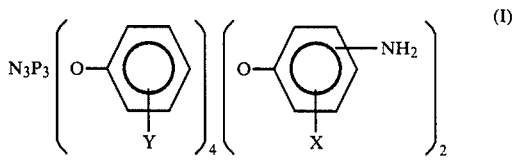

wherein X and Y are each independently selected from Cl, Br, F and H; and

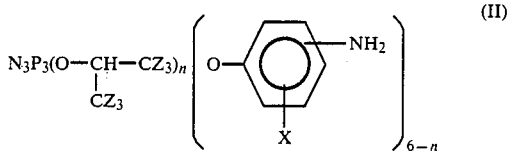

(II)

wherein n is a whole integer which is ≧1 and ≦5, each Z constituent is independently selected from F and H, and wherein X is Cl, Br, F or H. Due to the lower carbon content of the isopropoxy constituent, as compared to a phenoxy constituent, increased flame retardency in flexible foam compositions is probable.

In the process of this invention, the particular inert, organic solvent used is not critical. The solvent need only be inert in the reaction system and be capable of solubilizing the reactants under reaction conditions. For example, solvents such as octane, heptane, hexane, cyclohexane, benzene, toluene, xylene, diglyme, triglyme, tetraglyme, triethylamine, pyridine, tetrahydrofuran and dioxane are all suitable. To achieve convenient temperature control, the process of this invention is preferably run at reflux conditions and, thus, in these preferred cases, the solvent used is one which will provide reflux at the chosen process temperature. A preferred solvent is tetrahydrofuran as it provides good solubility and reflux at a temperature of from about 60° C. to about 70° C.

The use of a single selected inert organic solvent in the various reactions described herein is beneficial as the reflux temperature for the R-chlorocyclotriphosphazene aminophenoxide salt reaction can then be reasonably predicted. If several solvents are used, the reflux temperature of the ultimate reaction mix may not be so predictable, thus, resulting in an inability to use refluxing as a temperature control method to maintain the reaction temperature at a specified point. If refluxing is not used as a temperature control method, then solvent mixes may be used provided that no reaction, appreciable heat of solution, etc., results from the use of the solvent mix.

The subject process is generally run within the temperature range of from about 50° C. to about 140° C. High yields are obtained when the process temperature is within the range of from about 60° C. to about 70° C. Temperatures substantially lower than 50° C., e.g., 0° C., may very well produce the aminophenoxycyclotriphosphazene product sought; however, the yield is predicted to be low and reaction times long. Temperatures much in excess of 140° C. are not desirable as it is expected that some inter- and intramolecular cross-linking will occur. Such cross-linking lowers the yield of the aminophenoxycyclotriphosphazene product. When temperatures above 70° C. are used, it is preferred that the process be initiated at a lower temperature, say about 20° C. to about 50° C., followed by the raising of the temperature up to the selected level. By providing such a temperature profile over process time, the formation, during the initial phase of the process, of undesirable cross-linked products is avoided.

The reaction time for the process of this invention should be sufficiently long to achieve the desired aminophenoxy substitution of the chloride constituents initially present in the R-chlorocyclotriphosphazene reactant. The rate of aminophenoxy substitution is interrelated with process temperature. After process initiation, the higher the temperature used, the shorter the reaction period will be. Generally speaking, for the temperature range of 50° C. to 140° C., the reaction period will be about 200 hours for the lower end of the range to about 50 hours for the upper end of the range. For the temperature range of 60° C. to 70° C., the reaction period will be within the range of from about 170 hours to about 70 hours.

While the subject process is preferably run under reflux conditions, it is to be understood, that reflux conditions need not be used, but instead, can be replaced by other temperature control techniques, such as by reactor immersion in a controlled temperature bath.

The order of addition of the R-chlorocyclotriphosphazene and aminophenoxide salt reactants is not critical. However, agitation, e.g., stirring, is useful in ensuring uniformity of reactant concentrations in the reaction mix.

The determination of a minimum molar ratio of the R-chlorocyclotriphosphazene to the aminophenoxide salt is dependent upon the chloride content of the former. As there are 6-n chlorides in the phosphazene reactant, the minimum molar ratio of phosphazene reactant to aminophenoxide salt needed to give some yield of the isopropoxy- or phenoxyaminophenoxycyclotriphosphazene product is 1:a, wherein a is greater than 5-n. Since reaction yield is determinative of process efficiency, a molar ratio of 1:6-n, which ratio provides the minimum amount of aminophenoxy radicals needed to replace all of the chlorides in the phosphazene reactant, is preferred. Generally, a slight molar excess, say, 1 mole percent to about 10 mole percent, of aminophenoxide salt will be used to ensure complete chloride substitution. Molar ratios between 1:6-n and 1:5-n can be used to produce mixes of partially chloride substituted and completely chloride substituted isopropoxy- or phenoxy-aminophenoxycyclotriphosphazene product. Such mixes may provide the property sought and thus, in these cases, the further chloride substitution may not represent a correct economical choice.

The R-chlorocyclotriphosphazene reactant has the formula:

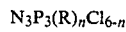

wherein R and n are defined as above.

Exemplary of such reactants are: isopropoxy-pentachlorocyclotriphosphazene; tri(1,1,3,3-tetrafluoroisopropoxy)-trichlorocyclotriphosphazene; tri(1,1,1,3,3,3-hexafluoroisopropoxy)-trichlorocyclotriphosphazene; triisopropoxy-trichlorocyclotriphosphazene; tetraisopropoxydichlorocyclotriphosphazene; diphenoxy-tetrachlorocyclotriphosphazene; triphenoxy-trichlorocyclotriphosphazene; tetraphenoxy-dichlorocyclotriphosphazene; pentaphenoxymonochlorocyclotriphosphazene; tri(o-chlorophenoxy)trichlorocyclotriphosphazene; tetra(p-chlorophenoxy)dichlorocyclotriphosphazene; penta(m-bromophenoxy)monochlorocyclotriphosphazene; di(p-fluorophenoxy)tetrachlorocyclotriphosphazene; and the like.

The aminophenoxide salt reactant has the formula:

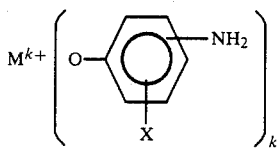

wherein $M^{k+}$ is an inorganic cation, preferably a metal, k is either 1 or 2, and X is Cl, Br, F or H. Preferred metal cations are those of Mg, Ca, Na, K and Li. Exemplary of suitable salts are: Sodium p-aminophenoxide; potassium m-aminophenoxide; calcium o-aminophenoxide; sodium p-chloro-m-aminophenoxide; magnesium o-bromo-p-aminophenoxide; lithium m-fluoro-o-aminophenoxide; potassium p-chloro-o-aminophenoxide and the like. Preferred aminophenoxide salts are sodium m-aminophenoxide and sodium p-aminophenoxide.

The R-chlorocyclotriphosphazene can be conveniently prepared in accordance with the following reaction:

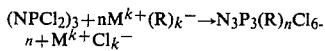

wherein n, k, $M^{k+}$ and R are as defined previously. The reaction occurs at a temperature within the range of from about 0° C. to about 150° C. and in the presence of an inert organic solvent. The $M^{k+}Cl_k^-$ salt will form a precipitate and be filtered from the reaction mix. To ensure that the hexachlorocyclotriphosphazene is not subjected to a molar ratio of hexachlorocyclotriphosphazene to $M^{k+}R_k^-$ salt less than 1:n, the $M^{k+}R_k^-$ salt is added slowly to the reaction mix with the reaction mix being continuously agitated, such as by stirring. The reaction is preferably run at reflux conditions so as to conveniently control the reaction temperature. With a reaction temperature above 60° C., the reaction time is about 0.5 hours to about 36 hours.

The $M^{k+}R_k^-$ salt is conveniently prepared by the reaction of ROH with a base, such as NaH, to yield the salt and water. The salt can also be purchased commercially. For example, the isopropoxide salt can be purchased from Morton Thiokol (Alfa), Inc.

The aminophenoxide salt reactant can be prepared in accordance with the reaction:

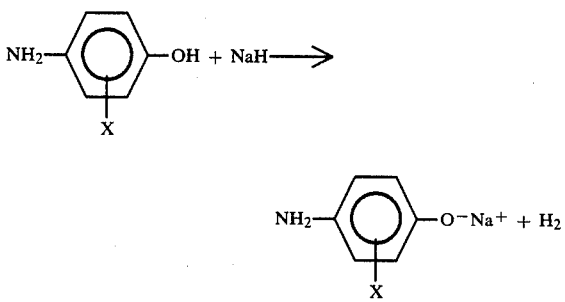

This reaction occurs in an inert organic solvent, which solvent is preferably the same solvent which is used in the R-chlorocyclotriphosphazene aminophenoxide salt reaction. The reaction mix should be agitated, e.g., stirred, and is preferably run under reflux conditions. The order of addition of the reactants is not critical. The reaction temperature is within the range of from about 0° C. to about 150° C. and the reaction runs for that period of time necessary to ensure complete reaction of the aminophenol reactant. Such reaction time is preferably from about 0.5 hours to about 24 hours. The base should be at least equimolar to the aminophenol reactant and is preferably used in excess. Such a molar ratio between the base and the aminophenol is important because, if there is any aminophenol contamination of the aminophenoxide salt, the aminophenol presence results in the production of aminol derivatives of R-chlorocyclotriphosphazene rather than the desired aminophenoxy derivatives. This is believed to be due to the faster rate of reaction between aminophenol and R-chlorocyclotriphosphazene than is the case for the aminophenoxide salt. Even further, formation of the aminol derivative results in acid production which neutralizes the aminophenoxide salt and results in production of even more aminophenol.

The following examples are submitted for the purpose of further illustrating the nature of the present invention and are not to be construed as a limitation on the scope thereof.

The NMR spectroscopy used in analyzing the reaction products in various of the following Examples was 31P NMR spectroscopy. In general, the instrument, a JEOL 90X FT NMR, was locked onto acetone-d6, and the shift of 85% $H_3PO_4$ set to zero. Samples were analyzed in THF solution with a coaxial tube containing acetone-d6.

All spectra exhibited AB2 systems, the appearance of which varies, depending on the ratio of coupling constant, J, to chemical shift difference, v, as described in "Applications of Nuclear Magnetic Resonance Spectroscopy in Organic Chemistry," L. J. Jackman, S. Sternhell, Pergamon Press, London, 1969, pp. 130–132; "Organic Spectroscopy—An Introduction," S. F. Dyke, A. J. Floyd, M. Sainsbury, R. S. Theobald, Penguin, England, 1971, pp. 120–122; and "Nuclear Magnetic Resonance," W. W. Paudler, Allyn and Bacon, Boston, 1971, pp. 115–120. The chemical shifts gave good correlation with shifts reported for similar aminophosphazenes in "Phosphorus-Nitrogen Compounds," H. R. Allcock; Acad Press, New York, 1972; and "The Chemistry of Phosphorus," J. Emsley, D. Hall, Harper and Row, London, 1976, p. 82.

EXAMPLE 1

Sodium aminophenoxide reactant was prepared by slowly adding sodium hydride (100%, 2.6 g, 0.11 mole) to a slurry of p-aminophenol (10.9 g, 0.1 mole) in about 100 mL tetrahydrofuran (THF). The reaction mixture was heated at 60°–67° C. for 3 hours, or until evolution of hydrogen was no longer visible. Sodium aminophenoxide salt, a purplish solid, formed during this time. The salt was either filtered and washed with THF, or used as prepared, as a slurry. The entire procedure was carried out under nitrogen.

The sodium phenoxide reactant was prepared by dissolving phenol (18.8 g, 0.2 mole) in 150 mL THF, and 100% sodium hydride (5.0 g, 0.21 mole) added slowly over 0.5 hr, with stirring, under nitrogen. The reaction was allowed to proceed until evolution of hydrogen was no longer apparent (about 0.5–1 hr). The resulting sodium phenoxide containing solution was usually clear and yellow, but sometimes a clear blue solution was obtained. Whatever the cause of this difference in color, subsequent reactions were unaffected.

The sodium phenoxide containing solution was added dropwise to a solution of hexachlorocyclotriphosphazene, (NPCl$_2$)$_3$ (17.3 g, 0.05 mole) in THF (200 mL) with stirring, under nitrogen. An exothermic reaction occurred as precipitation of a white solid (NaCl) took place. The reaction mixture was refluxed for about 3 hrs. The resulting mixture could be filtered, giving a THF solution of tetraphenoxy-dichlorocyclotriphosphazene as the filtrate, and NaCl as the filtered residue, or used as is. The weight of NaCl isolated after filtration and washing with THF was essentially quantitative (about 7.4 g in this case).

The tetraphenoxy-dichlorocyclotriphosphazene containing solution or slurry was combined with the above prepared sodium aminophenoxide, all at once, with stirring under nitrogen. A tan solid precipitated from the mixture, which was heated at 60°–67° C. for 2 days. The mixture was filtered, and the filtrate evaporated at reduced pressure to give an amber/red oil. Thin-layer chromatography showed the presence of two major products. 31P NMR spectroscopy showed that the major product was the desired compound, tetraphenoxy-bis(aminophenoxy)phosphazene, and that the product mix contained about 30% intermediates. The spectroscopy also showed overlapping AB2 systems. The desired compound, tetraphenoxy-bis(aminophenoxy)phosphazene, gave a peak at −8.9 ppm. The appearance of the spectrum was exactly as would be expected for a high ratio of J/v. The ratio was high due to the similarity of substituents on the P nuclei, which makes the chemical shift difference, v, small. The other two systems seen were due to chloride containing intermediates, as evidenced by peaks below −19 ppm.

EXAMPLE 2

The procedures of Example 1 were repeated except that the following quantities were used: hexachlorocyclotriphosphazene, 34.5 g (0.1 mole); phenol, 37.6 g (0.4 mole); 100% sodium hydride, 9.6 g (0.4 mole); aminophenol, 21.8 g (0.2 mole); 100% sodium hydride, 4.8 g (0.2 mole). The amount of sodium chloride filtered from the preparation of the tetraphenoxy-dichlorocyclotriphosphazene was 24.9 g (expected: 23.2 g), indicating a slight loss of adsorbed phosphazene. The hot slurry of sodium aminophenoxide was poured into the solution of dichloro-tetraphenoxycyclotriphosphazene. The mixture was heated with stirring under nitrogen at 60°–67° C. for 72 hours. The solid precipitate was filtered off: wt. 13.2 g (expected NaCl = 11.6 g).

Portions of the solid were analyzed by titration with acid, and extraction with acetone. The subsequent results were extrapolated to give data for the entire amount of solid. Thus, titration indicated the presence of 0.0035 moles of unreacted aminophenoxide; i.e., more than 95% of the added aminophenoxide underwent reaction. Extraction with acetone showed that 0.75 g of soluble material was present in the solid precipitate. Thus, the weight of solid precipitate due to NaCl was 12.8 g. This is within the accuracy of the weighing and titration techniques used, and indicates that the yield of the reaction was 95% or greater.

The filtrate was evaporated at reduced pressure to give a brown oil, which was dissolved in chloroform (total volume about 350 ml). Thin-layer chromatographic analysis of the solution revealed traces of aminophenol. The chloroform solution was extracted with great difficulty owing to emulsion formation with water (total volume about 300 ml) containing some potassium hydroxide. Thin-layer chromatography showed the absence of aminophenol.

The solution was dried over magnesium sulfate, filtered, and the solvent evaporated at reduced pressure, to give 60 g of brown/amber oil. The corresponding yield was 83%.

The mass spectrum of the final product showed a molecular ion at m/e 723, corresponding to the expected molecular weight of tetraphenoxy-bis(aminophenoxy)cyclotriphosphazene.

EXAMPLE 3

The same procedures were followed as in Example 1, with the following modifications. Reagent quantities: phenol, 74.4 g (0.8 mole); sodium hydride, 20 g (0.84 mole); hexachlorocyclotriphosphazene, 69 g (0.2 mole); aminophenol, 43.6 g (0.4 mole). The reaction time of sodium aminophenoxide with tetraphenoxy-dichlorocyclotriphosphazene was 168 hrs. at 60°–67° C. NMR analysis of the reaction mixture at this time showed the absence of chloride containing intermediates, indicating a quantitative yield of product was present.

The reaction mixture was washed with 350 ml water (in 3 batches), and the aqueous layers extracted with THF. The THF solutions were combined, dried over magnesium sulfate, filtered, and the solvent evaporated at reduced pressure, to give the brown oil; 131 g (91% yield).

The aqueous washings above were neutral to litmus paper, indicating complete absence of unreacted aryloxides.

EXAMPLE 4

The same procedures were followed as in Example 1. The reagent amounts were: phenol, 28.2 g (0.3 mole); sodium hydride, 7.4 g (0.31 mole); hexachlorocyclotriphosphazene, 34.5 g (0.1 mole); p-aminophenol, 32.7 g (0.3 mole); sodium hydride, 7.4 g (0.31 mole).

Thin layer chromatographic analysis of the final reaction mixture showed the absence of aminophenol, and the water wash sequence, including formation of the chloroform solution, was therefore omitted. Evaporation of the dried and filtered reaction mixture yielded 70 g of a reddish-orange oil (95% yield). Infrared analysis revealed the presence of a small amount of THF. The oil was subjected to several precipitation steps, wherein a THF solution of the oil was added to water/methanol mixtures, blended, and eventually filtered, to give a brown solid. Thin-layer chromatographic analysis showed that the initial oil was the same as a THF solution of triphenoxy-tris(aminophenoxy)cyclotriphosphazene obtained from Shin-Nisso Corp., which had been prepared by the known literature procedure as taken from the Kumar references. 31P NMR analysis showed that the compound was purer than the above sample. The infrared spectra of both materials were essentially identical.

EXAMPLE 5

The procedures of Example 1 were followed, using the following reagent quantities: phenol, 14.1 g (0.15 mole); sodium hydride, 3.8 g (0.16 mole); hexachlorocyclotriphosphazene, 17.25 g (0.05 mole); aminophenol, 16.2 g (0.15 mole); sodium hydride, 3.8 g (0.16 mole).

The final reaction was heated in THF at 60°–67° C. for 168 hrs. Water (300 ml) was added to the mixture. The aqueous layer was neutral to pH paper. The THF was evaporated to dryness, and the resulting aqueous slurry extracted with 2 × 300 ml chloroform. The chloroform extracts were dried over magnesium sulfate, filtered, and the solvent evaporated at reduced pressure to give a triphenoxy-tris(aminophenoxy)phosphazene containing brown oil: 36 g (97% yield).

The blending/precipitation procedure was carried out as in Example 4 to give 30.6 g of tan/brown solid. The yield of solid, even with losses incurred to the blender, and methanol/water precipitation, was 30.6 g, 83%.

The mass spectrum of the final product showed a molecular ion at m/e 738, as expected for triphenoxy-tris(aminophenoxy)cyclotriphosphazene.

EXAMPLE 6

Tetraisopropoxy-bis(aminophenoxy)cyclotriphosphazene was prepared using generally the same procedures of Example 1.

The sodium aminophenoxide salt (28 g, 0.2 mole) was prepared by the procedure of Example 1, using sodium hydride, 5.0 g (0.21 mole), and p-aminophenol, 21.8 g (0.2 mole). In a separate flask, sodium hydride (9.8 g, 0.41 mole) was slowly added to a solution of isopropanol (24 g, 0.4 mole) in THF (150 ml), and the reaction heated at 60°-67° C. for 18 hrs. The solution of isopropoxide was added to hexachlorocyclotriphosphazene (34.5 g, 0.1 mole) in about 150 ml THF, over a period of about one hour. An opaque suspension slowly formed, and the reaction was heated at 60°-67° C. for 3 hrs. The sodium aminophenoxide was slurried in about 300 ml THF and added to the reaction all at once. The resulting mixture was heated at 60°-67° C. for 3 days. A purplish suspension was obtained, to which 240 ml water was added, causing phase separation. The aqueous layer was separated, and titration with diluted HCl showed a negligible amount of unreacted base. The THF layer was dried over magnesium sulfate, filtered, and the solvent evaporated at reduced pressure to give tetraisopropoxybis(aminophenoxycyclotriphosphazene containing a brown oil. Thin-layer chromatography showed the absence of unreacted aminophenol. The NMR spectrum showed a major absorption centered at −12.6 ppm, which is the region expected for isopropoxyaminophenoxy phosphorus nuclei in cyclotriphosphazenes. The presence of chloride containing intermediates was evidenced by small peaks at −22 to −27 ppm. The size of the peaks showed that these constituted less than 5% of the product mix. The mass spectrum of the product showed a molecular ion at m/e 587, equivalent to the molecular weight of tetraisopropoxy-bis(aminophenoxy)cyclotriphosphazene, and the expected fragments were observed. A second fragmentation pathway was observed with a molecular ion at m/e 514, corresponding to tetraisopropoxy-monochloromono(aminophenoxy)phosphazene, the chloride containing intermediate.

EXAMPLE 7

The same procedures were followed as in Example 1, except that the following reagent amounts were used: sodium hydride, 3.8 g (0.16 mole); p-aminophenol, 16.2 g (0.15 mole); THF, 200 ml; sodium hydride, 3.8 g (0.16 mole); isopropanol, 9 g (0.15 mole); hexachlorocyclotriphosphazene, 17.25 g (0.05 mole). By placing the triisopropoxy-tris(aminophenoxy)cyclotriphosphazene containing brown oily product in a high vacuum for solvent evaporation, a dark red/brown solid was obtained.

The NMR spectrum was similar to that obtained for the product of Example 6, as described above.

I claim:

1. Compounds of the formula,

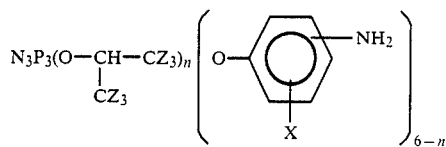

wherein n is either 3 or 4, each Z constituent is selected from F and H, and wherein X is selected from Cl, Br, F and H.

2. The compounds of claim 1 wherein all Z and X constituents are H.

3. A process for the production of a cyclotriphosphazene of the formula,

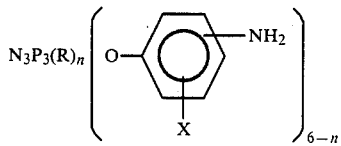

wherein R is an isopropoxy radical having the formula

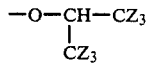

or an aryloxy radical having the formula

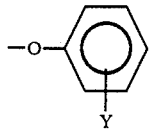

wherein each Z constituent is independently selected from F and H, wherein X and Y are each independently selected from Cl, Br, F and H, and wherein n is a whole integer which is $\geq 1$ and $\leq 5$, said process comprising, reacting an R-chlorocyclotriphosphazene having n R constituents and 6-n chloride constituents and an inorganic salt of aminophenoxide for a time period sufficient to yield said cyclotriphosphazene, said reaction occurring in an inert organic solvent medium, at a temperature within the range of from about 20° C. to about 150° C., and with a molar ratio of said R-chlorocyclotriphosphazene to said inorganic salt of aminophenoxide which is 1:a, wherein a is greater, than 5-n.

4. The process of claim 3 wherein said inorganic salt of aminophenoxide is an alkali metal aminophenoxide salt.

5. The process of claim 3 wherein said inorganic salt of aminophenoxide is a sodium aminophenoxide salt.

6. The process of claim 3 wherein the aminophenoxy constituent of said cyclotriphosphazene is m-aminophenoxy.

7. The process of claim 3 wherein the aminophenoxy constituent of said cyclotriphosphazene is p-aminophenoxy.

8. The process of claim 3 wherein said temperature is within the range of from about 50° C. to about 140° C.

9. The process of claim 3 wherein n is 3.

10. The process of claim 3 wherein n is 4.

11. The process of claim 3 wherein said molar ratio of said R-chlorocyclotriphosphazene to said inorganic salt of aminophenoxide is 1:6-n or above.

12. The process of claim 3 wherein R is an aryloxy radical.

13. The process of claim 3 wherein R is an aryloxy radical and Y is H.

14. The process of claim 13 wherein n is 3.

15. The process of claim 14 wherein said molar ratio of said R-chlorocyclotriphosphazene to said inorganic salt of aminophenoxide is 1:6-n or above.

16. The process of claim 13 wherein n is 4.

17. The process of claim 3 wherein R is an isopropoxy radical.

18. The process of claim 3 wherein R is an isopropoxy radical and all Z constituents are H.

19. The process of claim 18 wherein n is 3.

20. The process of claim 18 wherein n is 4.

21. The process of claim 20 wherein said molar ratio of said R-chlorocyclotriphosphazene to said inorganic salt of aminophenoxide is 1:6-n or above.

22. The process of claim 19 wherein said molar ratio of said R-chlorocyclotriphosphazene to said inorganic salt of aminophenoxide is 1:6-n or above.

23. The process of claim 20 wherein said molar ratio of said R-chlorocyclotriphosphazene to said inorganic salt of aminophenoxide is 1:6-n or above.

* * * * *

UNITED STATES PATENT AND TRADEMARK OFFICE
CERTIFICATE OF CORRECTION

PATENT NO. : 4,745,206

DATED : May 17, 1988

INVENTOR(S) : Massimo D. Bezoari

It is certified that error appears in the above-identified patent and that said Letters Patent is hereby corrected as shown below:

Column 4, line 44, delete "the".

Signed and Sealed this

Tenth Day of January, 1989

Attest:

DONALD J. QUIGG

*Attesting Officer*  *Commissioner of Patents and Trademarks*